(12) United States Patent
Holm et al.

(10) Patent No.: US 6,613,020 B1
(45) Date of Patent: *Sep. 2, 2003

(54) METHOD OF APPLYING A MIXTURE OF TWO LIQUID COMPONENTS AS WELL AS A DEVICE FOR CARRYING OUT THE METHOD

(75) Inventors: Niels Erik Holm, Birkerød (DK); Allan Garbasch, Birkerød (DK); John E. Fairbrother, Clwyd (GB); Frank Castellana, Skillman, NJ (US)

(73) Assignee: Bristol-Myers Squibb Company, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/761,466

(22) Filed: Dec. 6, 1996

(51) Int. Cl.[7] .................. A61M 5/00; A61M 37/00; A61B 17/08; B67D 5/52
(52) U.S. Cl. .................. 604/191; 604/82; 222/137; 606/214
(58) Field of Search ............. 239/86, 87, 92, 239/88, 89, 101, 270, 416.1, 418, 422, 589, 543, 113; 604/34, 43, 82, 191, 902, 151, 152, 153, 154–156, 73, 94, 131, 134–5, 173–181, 56, 187, 208, 214, 218, 224, 46, 49; 606/170, 214, 215, 92–94; 433/91, 95, 99, 100; 424/423; 222/137, 327, 391

(56) References Cited

U.S. PATENT DOCUMENTS

| | | |
|---|---|---|
| 3,223,083 A | 12/1965 | Cobey |
| 3,577,516 A | 5/1971 | Gould et al. |
| 4,359,049 A | 11/1982 | Redl et al. |
| 4,631,055 A | 12/1986 | Redl et al. |
| 4,735,616 A | 4/1988 | Eibl et al. |
| 4,846,405 A | 7/1989 | Zimmermann |
| 4,874,368 A | 10/1989 | Miller et al. ................. 604/82 |
| 4,902,281 A * | 2/1990 | Avoy ........................ 604/191 |
| 4,925,108 A | 5/1990 | Zimmermann |
| 4,978,336 A | 12/1990 | Capozzi et al. |
| 5,226,877 A * | 7/1993 | Epstein ....................... 604/35 |
| 5,336,170 A | 8/1994 | Salerno et al. ............... 604/24 |
| 5,350,084 A * | 9/1994 | Miller et al. ................ 222/137 |
| 5,368,563 A | 11/1994 | Lonneman et al. |
| 5,411,208 A | 5/1995 | Burgener |
| 5,582,596 A | 12/1996 | Fukunaga et al. .......... 604/191 |
| 5,605,255 A | 2/1997 | Reidel et al. |
| 5,605,541 A * | 2/1997 | Holm ........................ 604/82 |
| 5,656,035 A * | 8/1997 | Avoy ........................ 604/191 |
| 5,759,169 A | 6/1998 | Marx ......................... 604/82 |
| 5,759,171 A | 6/1998 | Coelho et al. ............... 604/82 |
| 6,331,172 B1 | 12/2001 | Epstein et al. |
| 6,461,325 B1 * | 10/2002 | Delmotte et al. |

FOREIGN PATENT DOCUMENTS

| | | | |
|---|---|---|---|
| EP | 0483759 | * | 5/1992 |
| EP | 0592242 | | 4/1994 |
| EP | 0634140 | | 1/1995 |
| WO | 9531137 | | 5/1995 |
| WO | 9619940 | | 12/1995 |
| WO | 9639212 | | 6/1996 |
| WO | 9619940 | * | 7/1996 |
| WO | 9639212 | * | 12/1996 |

* cited by examiner

*Primary Examiner*—Angela D. Sykes
*Assistant Examiner*—Patricia M. Bianco
(74) *Attorney, Agent, or Firm*—John M. Kilcoyne

(57) ABSTRACT

A novel device and method for applying two or more liquid components, for example fibrin sealant-forming components, comprises sources of the components fluid communication with, but remote from, an applicator for delivering the components to a desired site. Preferably, the user of such a device and method can actuate the application of the components by providing a signal to a controller which dispenses components from their sources to, and out of, the applicator. Greater ease, accuracy and control are realized by the user since the sources of components and controller are remote from the applicator and therefore not manually held by the user.

3 Claims, 3 Drawing Sheets

METHOD OF APPLYING A MIXTURE OF TWO LIQUID COMPONENTS AS WELL AS A DEVICE FOR CARRYING OUT THE METHOD

This application claims the benefit of U.S. Provisional Application No. 60/008,237, filed Dec. 7, 1995.

TECHNICAL FIELD

The present invention relates to a device and method for co-applying two or more liquid components from separate containers via separate liquid channels or tubes having separate outlets. In preferred embodiments the present device and method are useful for co-applying fibrin sealant components with a gas to form a spray.

BACKGROUND ART

U.S. Pat. No. 4,359,049 to Redl discloses a double barrel syringe for applying a tissue adhesive such as fibrin glue or fibrin sealant to a human or animal in need thereof. The fibrin sealant described comprises predominantly two major components, a fibrinogen-containing component and a thrombin-containing component, each in liquid form upon use. Essentially, the thrombin and fibrinogen, when mixed, provide that the peptide chains of the fibrinogen are cleaved and conditions are provided so that the resulting fibrin polymerizes into a clot which is useful for sealing fluid and air leaks, in haemostasis and to connect tissue. To avoid premature clot formation double-barrelled applicators are employed which, of course, keep the two components separate until application to a patient is required. The '049 patent discloses that pistons within the two cartridges, each containing one component, can be commonly actuated to dispense fluid simultaneously from each.

Other prior art patents describe various mixing heads for mixing two or more components used in these and other surgical sealants. For example, U.S. Pat. No. 5,116,315 assigned to Hemaldics describes a head where the liquid conducts leading from the component cartridge enter a mixing chamber fashioned so as to provide a swirling of the components before they exit a common exit channel. Adequate mixing of the components is desired so as to form a uniform fibrin sealant. Inefficient mixing results in the coadministration of fibrinogen and thrombin which may only result in a small yield of actual sealant. A difficulty with fibrin sealant applicators can be the premature formation of the clot within the device, especially those devices where the components are mixed within a mixing head and/or those devices wherein the components exit through a common channel. After the first spray of sealant is complete, a clot may block the exit channels rendering the applicator useless and greatly reducing the surgeon's flexibility in carrying out the sealant part of the surgical procedure.

U.S. Pat. No. 4,631,055 to Immuno includes a gas conveying channel for blowing a gas through the needle or mixing head during discharge of the components. However, an even, uniform distribution of the materials over the anatomical area of interest is still not achieved. Indeed, a significant amount of the components are wasted.

EP-PS No. 592,242 to Edwardson et al. discloses the first completely autologous fibrin sealant. It provides for the coadministration of a fibrin monomer solution with a buffer solution conducive to polymerisation of the fibrin monomer prepared in less than 30 minutes from a single source of blood (preferably that of the patient to receive the sealant). This break-through technology provides a fixed amount of fibrin monomer solution from a sample of about 140 to 160 ml of blood. Uniform and efficient mixing is even more important in order to benefit from this safe, efficient, autologous sealant product and therefore new devices and methods for applying two or more components to form a surgical sealant would be useful addition to the art.

PCT Application WO 96/17618 discloses a device and a method of applying components of a fibrin sealant. The device comprises a source of a gas and a reservoir for each component wherein the gas source and component reservoirs can be actuated by common means. Each of the reservoirs and gas source are separately in fluid communication with a spray head having a center aperture at its outlet end and annular apertures, arranged concentric with and radially outward from the centre aperture whereby the gas and each of said components are discharged through separate apertures. Preferably, the gas is discharged through the centre aperture and the fibrin sealant forming components are discharged separately through each of the annular apertures.

BRIEF DESCRIPTION OF THE INVENTION

In accordance with the present invention there is disclosed a method and device for utilizing a gas to co-apply two or more liquid components with enhanced uniformity of mixing of the components resulting in a more homogeneous mixture of the components and a minimal amount of unutilized components. The present device comprises a nozzle head having outlets out of which the liquid components and gas are dispensed and where the outlets are arranged in a straight line with the gas outlet at one end of that line. Also disclosed is a device and method for applying two or more liquid components, e.g., components which form a fibrin sealant, wherein the sources of said components, and preferably the source of a gas to be used, are in fluid communication with an applicator and are remote from that applicator.

In the present method, the flow rates of the components and gas are selected such that the two liquid components are drawn or sucked into the gas being expelled from the nozzle head as they exit their respective outlets of the nozzle head.

In this manner the two or more components are mixed outside the nozzle before they are sucked into the gas jet since the component exiting the outlet farthest from the gas outlet sucked across the outlet nearer to the gas outlet. The components are further mixed in the gas jet and the mixture and gas form a spray. In addition, the outlets are relatively small with the result that a relatively small amount of the components is exposed to the surroundings when the expelling is stopped. Furthermore, the clogging tendency in the outlets is substantially eliminated since there is no mixing of components in the nozzle head. Also the amount of the components remaining in said outlets after the application procedure is almost negligible. The latter factor is of vital importance in connection with a mixture of an autologous fibrin monomer solution and a buffer solution where the amount of fibrin monomer solution is relatively limited and accordingly must be utilized to an optimum.

When the components are discharged at mutually differing volume flows, it is according to the invention particularly advantageous to discharge the component with the lowest volume flow through the outlet accommodated farthest away from the gas jet. In this manner it is ensured that the component being discharged with the lowest volume flow is mixed with the component being discharged with the highest volume flow before said components enter the gas jet in the mixed state.

The expelling of the components through the nozzle head may according to the invention be carried out by means of an expelling means, which is activated by means of an electronic control unit, and the expelling of the gas may be carried out by means of a pump also activated by means of the electronic control unit, said electronic unit in turn being activated by means of a signaller controlled by the user handling the nozzle head. As a result, the expelling of the components and the gas can be carried out in a homogeneous manner at substantially constant volume flows.

In connection with a method using syringes with their respective expelling piston as containers for the components, the interruption of the expelling means through the control unit may according to the invention imply that the control unit activates said expelling means to retract the pistons of the syringes a short distance with the result that the components are retracted a short distance from the outlets of the nozzle. As a result, the risk of the two components coming into contact with one another and consequently the risk of a clogging of the nozzle outlets have been considerably reduced.

The invention relates furthermore to a device for applying a mixture of two liquid components kept in their respective containers, where said components are fed to a nozzle head through their respective liquid-transferring means, said nozzle head comprising a separate outlet channel for each component as well as a separate outlet channel for a gas fed through a gas-transferring means from a gas source, and where said device comprises an expelling means simultaneously activating the containers containing their respective component. The device according to the invention is characterised in that the component outlets and the gas outlet in the nozzle head are aligned along a substantially rectilinear line, the gas outlet being accommodated at one end of the line of outlets. Such a nozzle head is relatively easy to manufacture by way of any convenient means, e.g., injection moulding, and furthermore it ensures an efficient, good mixture of the components.

According to the invention the nozzle head may be supported by an elongated handle, and the component and gas-transferring means may be substantially resilient tubings which extend from said handle to a remote accommodation of the expelling means with the containers and the gas source, respectively. The resulting handling of the nozzle head is relatively easy and can be carried out without interference by the presence of the expelling means and the gas source.

Furthermore, the handle may according to the invention be associated with a push-button for actuation of the expelling means and the feeding of gas through a differential pressure-adjusting device. As a result, the component source containers, e.g., the pistons in the syringe cartridges, can be actuated to supply the gas and components without the presence of electricity adjacent the nozzle head and the associated handle.

When the containers used for the components are syringes with their respective piston for expelling the component in question, the expelling means may according to the invention comprise a holder for the securing of the syringes, and an electrically driven elevator means for a simultaneous actuation of the pistons of the syringes with the result that a particularly accurate and constant volume flow set in advance is obtained through each outlet in the nozzle upon such actuation.

Finally, it is according to the invention particularly preferred that the expelling means and the gas source in form of a gas pump are combined as a separate unit together with an electrically driven control unit, said control unit being adapted to control the expelling means and the gas pump at a signal from the user of the nozzle head.

BRIEF DESCRIPTION OF THE DRAWINGS

The invention is explained in greater detail below with reference to the accompanying drawing, in which.

DESCRIPTION OF THE PREFERRED EMBODIMENTS

Figure 1:
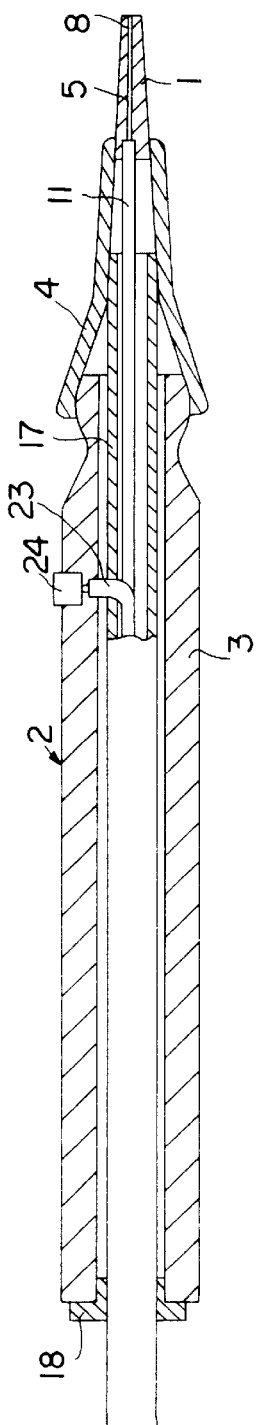
FIG. 1 shows a device according to the invention.
Figure 1:
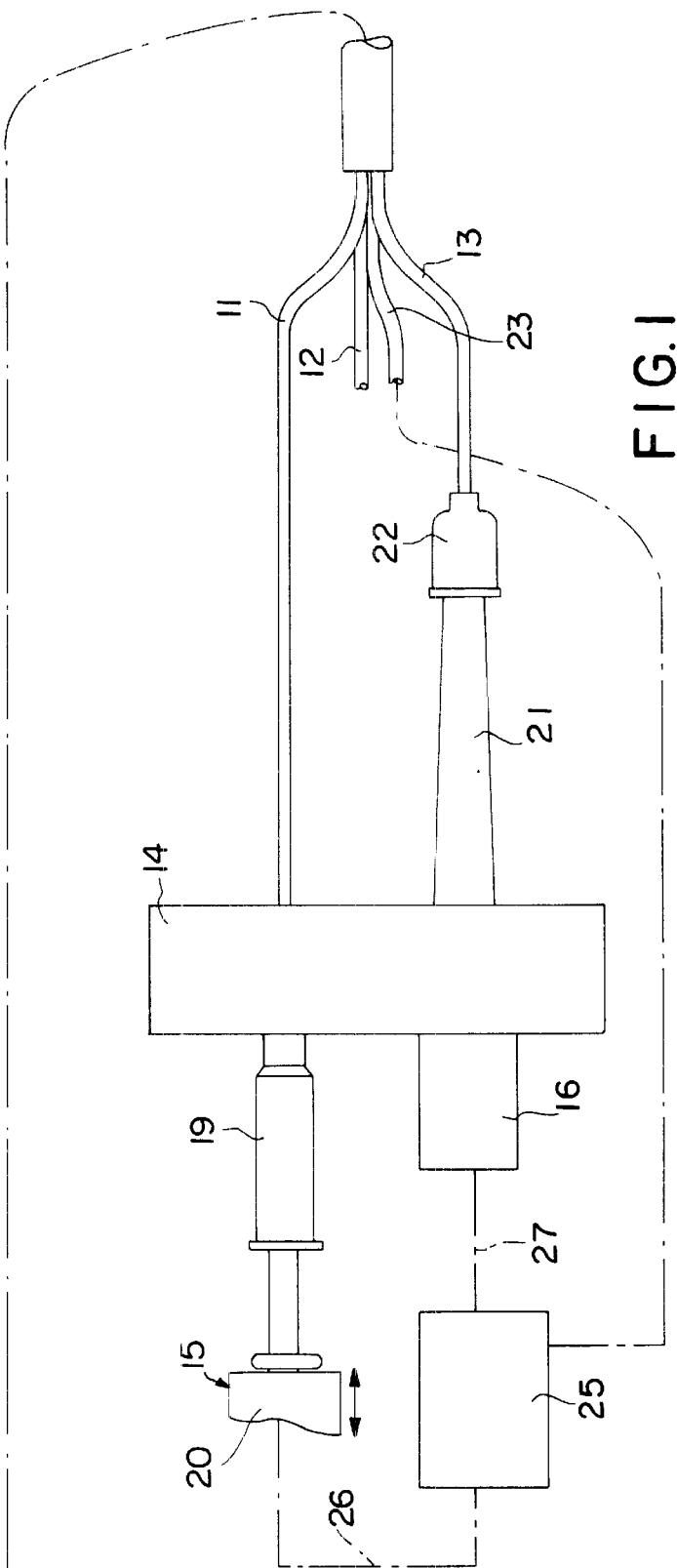

The device shown in FIG. 1 comprises a nozzle head 1 secured at the end of a handle designated the general reference numeral 2. This handle comprises a tubular body 3 connected through a transition portion 4 to the nozzle head 1, said tubular body 3, said transition portion 4, and said nozzle head 1, respectively, having a circular cross section. However, any convenient handle or means to hold or accommodate the nozzle head could be employed.

Figure 3:
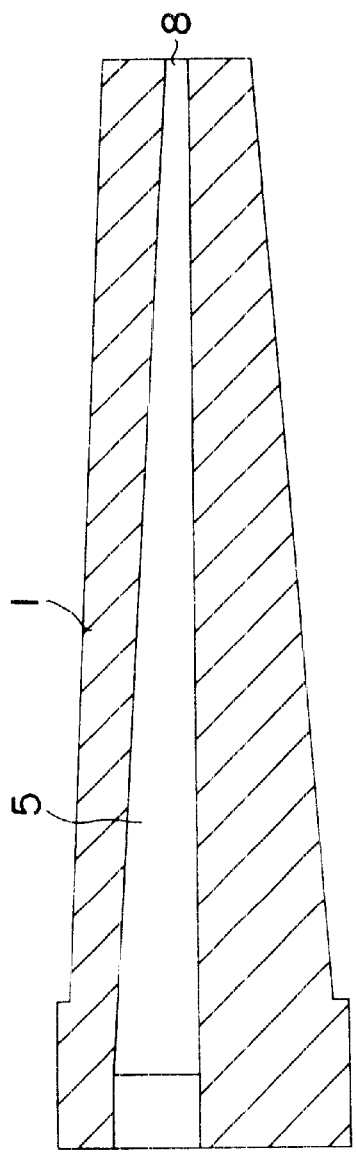
Figure 2:
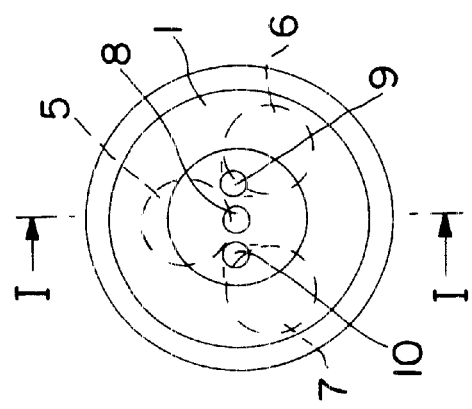
FIG. 2 is a front view of a nozzle head used in the device, and FIG. 3 the same taken along the lines I—I in FIG. 2.

As illustrated in particular in FIGS. 2 and 3, the nozzle head is preferably conically shaped with three through channels 5, 6, and 7, where two channels serve as outlet channels for two different components while the third channel serves as outlet channel for a gas. Of course, additional channels and outlets can be utilized as required by the particular material or product to be applied. The outlet channels 5, 6, and 7 are formed by any convenient means, e.g., by the nozzle head being molded in a suitable plastic material, such as polystyrene material, SAN. The outlet channels extend from their respective opening at the broadest end of the nozzle head 1 adjacent the handle 2, said openings being placed at the corners of an isosceles triangle, cf. the dotted lines of FIG. 2. At the corners of the isosceles triangle, each channel is of a diameter of approximately 1.2 mm, and preferably after a short distance with a substantially constant diameter each channel narrows down so as to be of the desired diameter at the opposite end. This is done to accommodate using fluid transfer tubing which may be larger in diameter than the desired outlet size. Any convenient diameter outlets can be utilized, but outlets having diameters of 0.3 mm to 0.5 mm and preferably 0.3 mm are preferred. At this end of the channels, the outlets are aligned along a rectilinear line with a center distance of approximately 0.5 mm. The outlets have been designated the reference numerals 8, 9, and 10, respectively, in FIG. 2.

The above short distance of a substantially constant inner diameter of the outlet channels 5, 6 and 7 in the nozzle head serves to receive the end of fluid transfer tubes 11, 12, and 13, respectively, which in turn are provided for the feeding of said components and said gas. These fluid transfer tubes 11, 12, and 13 extend axially through the handle 2 and forwards to a coupling plate 14, which is arranged and associated with an expelling means for the components and designated the general reference numeral 15, as well as a gas pump 16. The tubings 11–15 can be surrounded by a resilient protecting jacket 17. At the end of the handle 2 opposite the nozzle head 1, the protecting jacket 17 with the tubings 11–12 can be preferably retained in the handle 2 by means of a cap 18 inserted thereon. The cap 18 is provided with a central, through opening and co-operates with the protecting jacket 17 and is retained in said handle 2 by way of friction.

Figure 4:
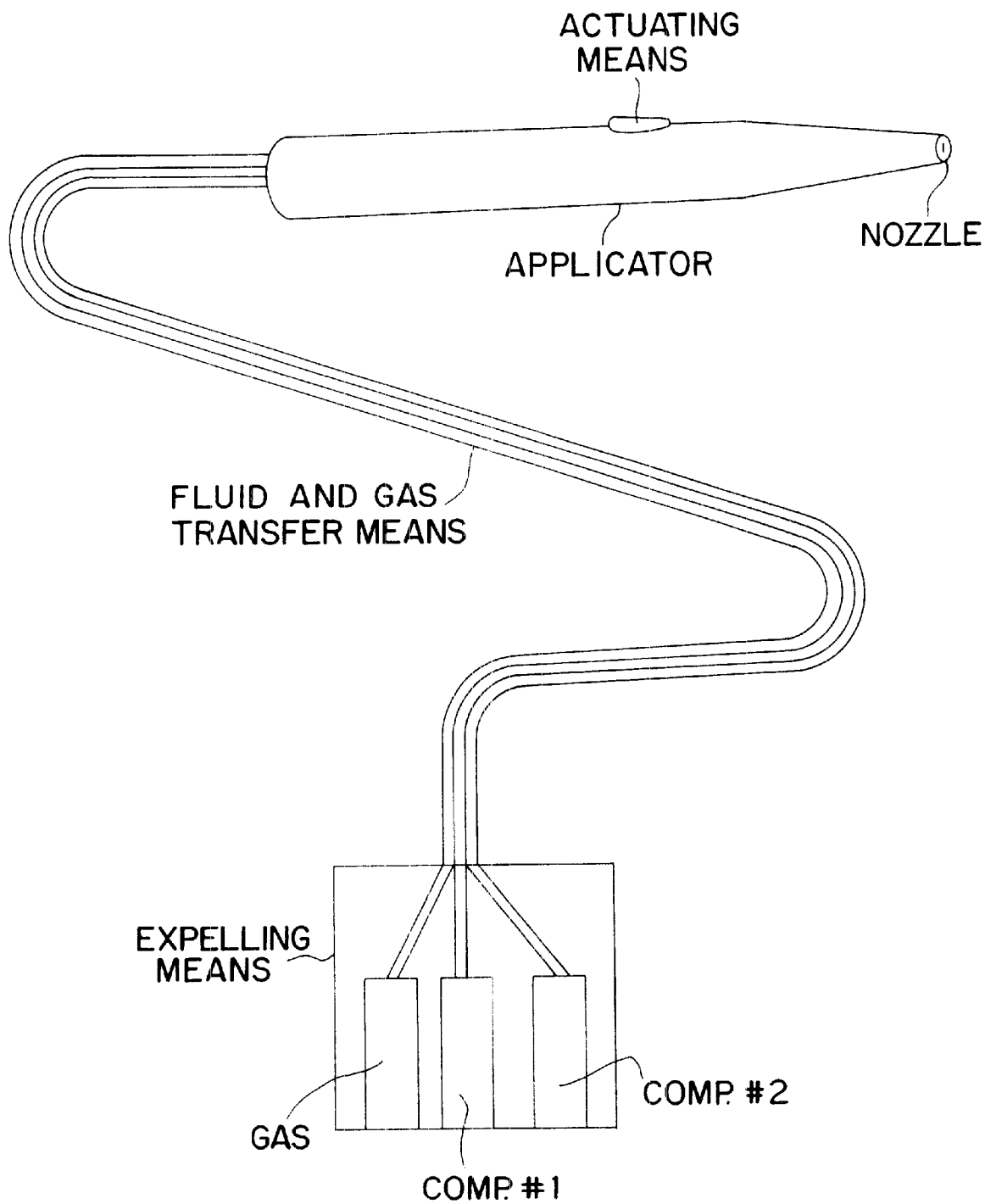
FIG. 4 shows another view of a device according to the invention.

As mentioned above, the preferred device according to this invention comprises a spray applicator or "pen" which is remote from, but in fluid communication with, the sources of liquid components and/or gas. In areas such as the application of fibrin sealants this provides a greatly improved tool for the surgeon. This is because the prior art fibrin sealant applicators all include the sources of components in the hand-held applicator. As discussed previously, prior art fibrin sealant applicators are typically double-barrel syringes attached to a Y-piece or mixing lead. This is generally an awkward instrument for the surgeon to control and even when the surgeon uses both hands, a less than desirable application is achieved. One embodiment of the device of this invention is set forth in FIG. 4.

The present spray applicator comprises a nozzle head with outlets and separate fluid transfer tubes for each component providing fluid communication between the outlets and the sources of components to be applied. Preferably, the nozzle head has a handle which can be an elongated "pen" accommodating the nozzle head at one end with the fluid transfer tubes extending therethrough, exiting the opposite end and continuing to said sources of components. The sources of components at the remote location, which can be in any convenient containers, e.g., syringe cartridges, are preferably part of an expelling means which dispenses or expels these components from the sources through the fluid transfer tubes and out of the outlets of the nozzle head, as desired by the operator or surgeon. This can be accomplished by any convenient means such as valves in the nozzle head or handle of the applicator or preferably by providing an actuating means which sends a signal to the supply unit upon actuation by the operator or surgeon. The actuating means can be a foot pedal or a button in the applicator as are known in the device art. In a preferred embodiment the actuating means is a resilient bladder positioned in the applicator and connected via a pressurized line to a signal means, such that upon depression of the resilient bladder by the fingertip or hand of the surgeon the signal means detects a difference in pressure and signals the supply unit to supply the components.

The gas used to co-apply the components can be also supplied from, and controlled by, the expelling means in a preferred embodiment or, can be supplied and/or controlled separately from the liquid components.

Returning to FIG. 1 in further describing the preferred expelling means, at the coupling plate 14, the fluid transfer tubes 11, 12 are inserted in their respective through bore (not shown), at the opposite end of which the tubings are adapted to be connected with their respective syringe 19 (or other convenient component source container) for their respective component. The drawing shows only one syringe 19 communicating with the tubing 11. The coupling plate 14 is adapted such that both the tubings 11 and 12 and the syringes, such as the syringe 19, can be easily removed. Beyond the latter coupling plate 14 for receiving the syringes 19, the expelling means 15 comprises an elevator means 20 for expelling the contents of the syringes 10.

As illustrated in FIG. 1, the third tubing 13 serves to feed the gas and is connected to the gas pump 16 through an outlet nozzle 21 and a luer coupling 22. The luer coupling 22 implies furthermore that the above tubing can be easily coupled to and removed from said coupling plate 14. A filter means is provided within the outlet nozzle 21.

As illustrated in FIG. 1, a fourth tubing 23 is furthermore accommodated inside the protecting jacket 17. The said fourth tubing 23 is at one end associated with a diagrammatically shown push-button 24 inside the handle 2, while the opposite end thereof is detachably connected to a control unit 25 in a manner not described in greater detail, said control unit being associated with the expelling means 15. When the push-button is pressed down, the tubing 23 with said push-button 24 and the control unit 25 is adapted to transfer the resulting pressure difference inside the tubing 23 as a signal to the control unit 25. As a result, the control unit initiates through the diagrammatically shown tubings 26, 27 the necessary activation of the elevator means 20 of the expelling means 15 and the air pump 16, respectively. The tubing 23 is detachably coupled to the control unit 25 in a manner not described in greater detail by means known to those skilled in the art.

The described device is mainly intended for application of a mixture of two or more components in, e.g., fibrin monomer and a buffer fluid with a pH of 10, respectively, as set forth in the aforementioned WO 96/17638 and EP 592,242. These two components are received in their respective syringe, such as the syringe 19, said syringes being dimensioned such relative to one another that the desired mixing ratio is established by a simultaneous activation of the pistons of the syringes by means of the elevator means 20. The mixing ratio of the pH 10-buffer to fibrin monomer is preferably 1 to 7, and usually a 5 ml syringe is used for receiving fibrin monomer and a 1 ml syringe for the pH 10-buffer. The tubings 11–13 are according to a preferred embodiment shaped by way of co-extrusion, the inner layer of the tubings being made of polyurethane which is inert to the fluids in question, and the outer layer of said tubings being made of polyurethane or PVC. The tubings are formed with an inner diameter of 0.3 mm with the result that a length of 2 m only allows approximately 0.3 ml of fluid to be received in each tubing, i.e., a total of 0.6 ml of fluids.

When the expelling means 15 and the air pump 16 are activated by the push-button 24 being pressed down, the two components are expelled from their respective outlet in the nozzle head 1 while the gas is simultaneously being expelled through the associated outlet in the nozzle head.

The gas is expelled through the outlet at one end of the row of outlets, while the component to be fed in the lowest amount, viz. the pH-buffer, is expelled through the outlet 9 provided at the opposite end. The other component, fibrin monomer, is expelled through the outlet 8 in the middle of the row of outlets. These components can be expelled at any convenient rate but low flow rates have been found to be advantageous. Accordingly, the pH 10 buffer can be expelled at flow rates between 0.0040 and 0.0100 ml/sec and the fibrin solution between 0.028 and 0.070 ml/secs preferably at the aforementioned 1:7 ratio. Most preferably, the fibrin monomer and pH 10-buffer to be mixed are expelled at a volume flow of approximately 0.04 ml/sec and 0.0057 ml/sec, respectively.

Air is used as gas in the preferred embodiment, said air being sucked in from the surroundings and subsequently carried from the pump 16 through a filter to the nozzle head 1. Alternatively, any source of desired gas can be employed. The speed of the air molecules must be relatively high at the same time as the amount of air used must be kept at a minimum. An outlet diameter of 0.3 mm has the effect that the volume flow of the air is approximately 1.25 l/min. during the expelling procedure, lower volume flow being preferred.

When the air and the two components flow out of their respective outlets, the fluids are sucked into the flow of air and are substantially atomized. The mixing of the two fluid components has been at least partially accomplished when said components are sucked into the flow of air. A lowering of the respective discharge speeds is carried out by an adjustment of the diameters of the outlets and their mutually distance in such a manner that both are as small as possible. In this manner it is possible to operate with relatively long tubings, i.e. the distance between the nozzle head 1 and the coupling plate 14 can be relatively long, such as for instance 2 m. The low discharge speeds render it possible to apply the liquid mixture in thin uniform layers with the result that a layer of a higher total thickness may be provided by laying more layers on top of each other.

The expelling of the components from the respective syringes is as mentioned carried out inside the expelling means 15 which forms a combined unit together with the control unit 25. Both the expelling means 15 and the control unit 25 are electrically driven. This unit may be placed relatively far away from the site where the mixture is to be applied, and it can be adapted for reuse, whereas the nozzle head with the handle 2 and tubings 11, 12, and 13 may be adapted to be disposable. The control unit 25 can be such that an interruption of the application procedure before the syringes 19 are empty can have the effect that the elevator means 20 retracts the pistons in the syringes 19 a short distance in such a manner that the fluids in question are sucked a short distance away from the outlets in the nozzle head 1. In this manner it is avoided that an interruption of the applying procedure involves a post-expelling caused by pressures accumulated in the walls of the tubings, and especially in optionally present air bubbles in the syringe containing fibrin I. The preferred retraction volume is approximately 0.04 ml, which corresponds to the expelling for 1 sec.

The described device renders it possible to apply a fluid mixture in a thickness of approximately 170 μm, which implies that an amount of 5 ml fibrin and a corresponding amount of pH 10-buffer can cover an area of 300 $cm^2$. In connection with a length of tubing of approximately 2 m, the total amount of lost fluid in said tubings is, as mentioned, approximately 0.3 ml, whereby the amount of not used components after the complete expelling from the syringe is relatively low.

The invention has been described with reference to a preferred embodiment of a device for dispensing a mixture of fibrin monomer and a pH 10-buffer. The mixing ratios used must ensure that the mixture is relatively neutral, and preferably said neutral state has already been achieved in the air before the application site has been reached. During the production procedure, the fibrin monomer in question has been admixed a coagulation-stopping agent with a pH-value of 4.6. The restoration of fibrin monomer to the neutral state implies that the coagulation process starts again.

The device in question can also be used for other components beyond fibrin I and pH 10-buffer, where the mixing ratios and the volume flows must be adapted to these components. For example, fibrinogen-containing components and components containing thrombin or a thrombin-like enzyme can also be applied using the instant device and method.

What is claimed is:

1. A system for applying two or more liquid components to a site in need thereof comprising a) a discrete source of each of said components;

b) an applicator for dispensing said components onto or into said site, said applicator comprising a spray head having discrete apertures therein through which said two or more liquid components can be dispensed, said apertures corresponding to discrete channels through said spray head;

c) tubing having discrete channels therein for the transfer of components to said spray head, said tubing and discrete channels at a first end being connected to and in fluid communication with said discrete channels within said spray head, said tubing at a second end being connected to, and in fluid communication with, d) means for expelling said components from said spray head; said means for expelling comprising a discrete source container for each of said components, said container having a slidable piston in a first end of said container such that appropriate displacement of said piston displaces an amount of component from a second end of said container; an elevator for displacing said piston a desired distance in a desired direction, said elevator being responsive to a controller which, in response to an actuating signal from a user, signals said elevator to displace said piston; and each of said discrete sources being connected to and in fluid communication with said discrete channels of said tubing, said means for expelling further including means for transferring said two or more components out of said sources through said discrete channels of said tubing and said spray head and out of said apertures in said spray head; whereby a user of said application system is able to apply said two or more components without the manual holding of said sources of components.

2. A device for applying two or more liquid components comprising a) a nozzle through which said components are delivered;

b) sources of said components in fluid communication with said nozzle;

c) a handle which, in cooperation with said nozzle, facilitates control of the direction of the application of said components and is remote from said sources of components; and d) and actuator in communication with a controller capable of facilitating delivery of said components from said sources to, and out of, said nozzle; wherein said actuator is in fluid or air communication with a pressure reading device via tubing such that when said actuator is pressed or actuated, a pressure differential is generated and the pressure reading device senses such pressure differential and actuates said controller in response to said pressure differential.

3. A system for applying two or more liquid components to a site in need thereof comprising a) a source of said components;

b) an applicator for dispensing said components onto or into said site; and c) a controller to control the expulsion of said components form said source to, and out of, said applicator means; wherein said source of components is in fluid communication with said applicator and is remote from said applicator such that a user can apply said components without manually holding said source; and further, wherein said source of said components are cartridges with pistons, and wherein expulsion of said components from said cartridges is accomplished by an elevator which pushes said pistons in response to said controller.

* * * * *